US010955409B2

(12) United States Patent
Ghetti et al.

(10) Patent No.: US 10,955,409 B2
(45) Date of Patent: Mar. 23, 2021

(54) METHOD FOR THE IDENTIFICATION OF SENSORY NEURON SUBTYPES IN EX VIVO PREPARATIONS

(71) Applicant: AnaBios Corporation, San Diego, CA (US)

(72) Inventors: Andrea Ghetti, San Diego, CA (US); Yannick Miron, San Diego, CA (US); Claudio Ghetti, Berkeley, CA (US); Paul Miller, San Diego, CA (US)

(73) Assignee: AnaBios Corporation, San Diego, CA (US)

( * ) Notice: Subject to any disclaimer, the term of this patent is extended or adjusted under 35 U.S.C. 154(b) by 156 days.

(21) Appl. No.: 15/957,770

(22) Filed: Apr. 19, 2018

(65) Prior Publication Data

US 2018/0306781 A1    Oct. 25, 2018

Related U.S. Application Data

(60) Provisional application No. 62/488,667, filed on Apr. 21, 2017.

(51) Int. Cl.
*G01N 33/50* (2006.01)
*C12N 5/0793* (2010.01)

(52) U.S. Cl.
CPC ....... *G01N 33/5058* (2013.01); *C12N 5/0619* (2013.01); *G01N 33/5005* (2013.01); *C12N 2500/12* (2013.01); *C12N 2500/14* (2013.01); *C12N 2500/32* (2013.01); *C12N 2501/13* (2013.01); *C12N 2529/00* (2013.01)

(58) Field of Classification Search
None
See application file for complete search history.

(56) References Cited

U.S. PATENT DOCUMENTS

2015/0301028 A1*  10/2015  Eggan ............... G01N 33/6872
                                                     435/29

OTHER PUBLICATIONS

Gemes "Failure of action potential propagation in sensory neurons: mechanisms and loss of afferent filtering in C-type units after painful nerve injury" J Physiol 591.4 (2013) pp. 1111-1131 (Year: 2013).*

(Continued)

*Primary Examiner* — Adam Weidner
(74) *Attorney, Agent, or Firm* — Entralta P.C.; James F. Fleming; Peter D. Weinstein

(57) ABSTRACT

The present invention provides methods of identifying and distinguishing different types of nerve cells in ex vivo cell culture, the method comprising the steps of: a) culturing somato-sensory nerve cells ex vivo, b) loading the nerve cells with a calcium, sodium, or voltage-sensitive indicator or expressing a genetically encoded calcium, sodium, or voltage-sensitive indicator, c) pulsing the nerve cells with an electrical train of bipolar square waves at two different voltages and two different frequencies; wherein the first voltage is 10 V/cm or less (low voltage) and the second voltage is between 12 and 20 V/cm (high voltage); and wherein the first frequency is 5 Hz or less (low frequency) and the second frequency is between 15 and 20 Hz (high frequency), and d) detecting activation of the nerve cell by measuring the changes in the signal intensity of the indicator, wherein low voltage and low frequency activation indicates a first type of cell and activation detected only at high voltage indicates a second type of cell.

11 Claims, 5 Drawing Sheets

(56) References Cited

OTHER PUBLICATIONS

Sengupta "Characterization of Mechanosensitive Pelvic Nerve Merent Fibers Innervating the Colon of the Rat" Journalofneurophysiology vol. 71, No. 6 (Year: 1994).*

Peterka "Imaging voltage in neurons" Neuron. Jan. 13, 2011; 69(1): 9-21 (Year: 2011).*

Jacobs "Control of Action Potential-Induced Ca21 Signaling in the Soma of Hippocampal Neurons by Ca21 Release from Intracellular Stores" Journal of Neuroscience, Jun. 1, 1997, 17(11):4129-4135 (Year: 1997).*

* cited by examiner

METHOD FOR THE IDENTIFICATION OF SENSORY NEURON SUBTYPES IN EX VIVO PREPARATIONS

CROSS REFERENCE TO RELATED APPLICATIONS

This application claims benefit of U.S. Provisional Application No. 62/488,667, filed on Apr. 21, 2017.

BACKGROUND

The subject of this patent application relates generally to drug discovery in the specific therapeutic area of pain and analgesia, and more particularly to a system and associated methods for predicting the selectivity of a drug candidate for different types of pain-conducting nerve fibers.

Applicant(s) hereby incorporate herein by reference any and all patents and published patent applications cited or referred to in this application.

Pain management continues to be a major unmet medical need. A large number of patients affected by various forms of chronic neuropathic pain do not receive any benefits from the current medications while other patients only obtain limited relief from the use of these drugs. Many developed drugs have either been discovered by accident or by observation. Furthermore, several of the current therapeutic options are associated with serious side effects and/or risk of addiction, as is the case for opioid-based drugs. Another common class of drugs used for treatment of neuropathic pain (anti-epileptics) can induce serious central nervous system-related side effects like drowsiness, somnolence, loss of consciousness as well as cardiac side effects. Patients also respond to these treatments differently, possibly because of gender differences or genetic backgrounds. Efforts are currently underway to develop novel pain drugs that are devoid of serious side effects and that can provide more significant pain relief to a broader patient population.

A further complicating factor in pain drug discovery is the fact that pain pathologies can be very diverse and different pain conditions will very likely require a variety of tailored therapeutic agents. For example, pain associated with postherpetic neuralgia, diabetic painful neuropathy and fibromyalgia may need three different type of drugs. It is therefore of the utmost importance to be able to generate preclinical data that can reliably predict the specific action of new drugs on the human pain pathway and provide information as to which pain type may be best treated by a given drug candidate. Over the last several years, important progress has been made in the field of clinical diagnostic neurology. Thanks to the introduction of a variety of tests conducted on patients, it is possible to begin establishing with some accuracy the type of somato-sensory nerve fiber(s) affected by a painful pathology and, in some cases, even assess the extent and type of damage. This information can be very valuable for guiding the selection of the treatment options.

One class of data that can be obtained by patient's examination relates to the specific types of somato-sensory fibers that are affected by the painful pathology. In general, somato-sensory information is carried from the periphery of the body to the central nervous system by three main types of nerve fibers. The three fibers types are commonly distinguished based on their diameter, the extent of myelination and the conduction velocity. Among somato-sensory pathways, A$\delta$- fibers have the largest diameter, the most extensive myelination and faster conduction velocity. These fibers typically carry non-pain-related, proprioceptive information. The A$\delta$- fibers have smaller diameter compared to the A$\beta$, have thinner myelination and slower conduction velocity. A$\delta$-fibers conduct nociceptive information and their activation is associated with the perception of pain. The last fiber type, is the C-type. These fibers have the smallest diameter, are not myelinated and exhibit the slowest conduction velocity among sensory fibers. The activation of C fibers is also associated with pain perception.

Numerous methods have been employed to profile the specific pathophysiology of individual pain patients. These methods rely on a variety of peripheral stimuli which include: electrical shocks, chemical irritants, laser-induced heating, vibrations, cooling and pin pricks. In one version of these kind of studies, a tight cuff induces the block of nerve impulses conduction along the myelinated fibers and allows for the study of the selective contribution of C-fibers to the pain state. In other cases, the preferential activation of C fibers or A$\delta$ fibers can be obtained by adjusting the temperature of a stimulus probe or using mechanical stimulation with probes of different geometries. In addition, several groups have shown that sine-wave current electrical stimulation can be used to establish the current perception threshold and track how this is affected in pathological states associated with pain. Furthermore, standardized methods have been developed based on an apparatus that delivers controlled sine-wave stimuli and allows for the selective activation of C, A$\delta$- or A$\delta$-type fibers. These methods rely on the differential activation of the different fiber types when sine-wave stimulation is delivered at frequencies of 5, 250 and 2000 Hz. These different stimulations are associated with tingling or low intensity pain perception in human subjects and studies conducted in human volunteers and animal models have established that the somatic stimulation at 5 Hz induces perceptions largely mediated by C-type fibers, while the 250 Hz and 2000 Hz stimulations elicit sensory perceptions mediated by A$\delta$- and A$\delta$-fibers respectively.

The frequency-dependent classification of different fiber types relies on the diverse biophysical properties of the various fibers. Theoretically, a number of membrane properties can determine the firing frequency of nerve fibers: input resistance, membrane time constant, resting potential, the activation threshold and activation time constant of ion channels embedded in the membrane, the voltage and frequency dependence of ion channel inactivation and the time constant of recovery from inactivation. In addition, in clinical settings, the density of different nerve terminals in the specific somatic region where the testing electrodes are positioned, can impact the ability of the subject to perceive different kinds of electrical stimuli.

A methodology that allowed the identification of A$\delta$- and C-type cells in ex vivo preparations of sensory neurons, would be highly valuable as it would allow to identify the specific activity profile of new drug candidates. This information could then be used to develop clinical trial plans that match specific pain conditions with the right drug. Absent this information, it is extremely difficult to decide the most appropriate therapeutic use of a new potential analgesic given that many types of pain exist, each with a distinct pathophysiological mechanism.

The present invention describes a device and a method that allows for the identification of A$\delta$- and C-type cells in ex vivo isolates of sensory neurons. The method entails the use of field electrical stimuli to differentially activate the cells from the different cell classes, based on their sensitivity to varying intensity and frequency of the electrical stimulation.

SUMMARY OF THE INVENTION

In one aspect, the present invention provides a method of identifying and distinguishing different types of nerve cells in ex vivo cell culture, the method comprising the steps of: a) culturing somato-sensory nerve cells ex vivo, b) loading the nerve cells with a calcium, sodium, or voltage-sensitive indicator or expressing a genetically encoded calcium, sodium, or voltage-sensitive indicator, c) pulsing the nerve cells with an electrical train of bipolar square waves at two different voltages and two different frequencies; wherein the first voltage is 10 V/cm or less (low voltage) and the second voltage is between 12 and 20 V/cm (high voltage); and wherein the first frequency is 5 Hz or less (low frequency) and the second frequency is between 15 and 20 Hz (high frequency), and d) detecting activation of the nerve cell by measuring the changes in the signal intensity of the indicator, wherein low voltage and low frequency activation indicates a first type of cell and activation detected only at high voltage indicates a second type of cell.

In another aspect, the present invention provides a method of identifying and distinguishing Aδ-type nerve cells and C-type nerve cells in ex vivo cell culture, the method comprising the steps of: a) culturing somato-sensory nerve cells ex vivo, b) loading the nerve cells with a calcium, sodium, or voltage-sensitive indicator or expressing a genetically encoded calcium, sodium, or voltage-sensitive indicator, c) pulsing the nerve cells with an electrical train of bipolar square waves at two different voltages and two different frequencies; wherein the first voltage is 10 V/cm or less (low voltage) and the second voltage is between 12 and 20 V/cm (high voltage); and wherein the first frequency is 5 Hz or less (low frequency) and the second frequency is between 15 and 20 Hz (high frequency), and d) detecting activation of the nerve cell by measuring the changes in the signal intensity of the indicator, wherein low voltage and low frequency activation, or low voltage and high frequency activation indicates the nerve cell is a Aδ-type nerve cells and activation detected only at high voltage indicates the nerve cell is a C-type nerve cell.

In yet another aspect, disclosed herein is a method of identifying a drug candidate selective for a Aδ-type nerve cell or a C-type nerve cell, the method comprising the steps of: a) culturing somato-sensory nerve cells ex vivo, b) loading the nerve cells with a calcium, sodium, or voltage-sensitive indicator or expressing a genetically encoded calcium, sodium, or voltage-sensitive indicator, c) pulsing the nerve cells with an electrical train of bipolar square waves at two different voltages and two different frequencies; wherein the first voltage is less than 10 V/cm (low voltage) and the second voltage is between 12 and 20 V/cm (high voltage); and wherein the first frequency is less than 5 Hz (low frequency) and the second frequency is between 15 and 20 Hz (high frequency), d) detecting activation of the nerve cell by measuring the changes in the signal intensity of the indicator, e) contacting an identified nerve cell with a drug candidate, and f) determining if the drug candidate selectively modulates the identified nerve cell, thereby identifying a drug candidate selective for a Aδ-type nerve cell or a C-type nerve cell, wherein low voltage and low frequency activation, or low voltage and high frequency activation indicates the nerve cell is a Aδ-type nerve cells and activation detected only at high voltage indicates the nerve cell is a C-type nerve cell.

In another aspect, disclosed herein is a method of identifying and distinguishing Aδ-type nerve cells and C-type nerve cells in ex vivo cell culture, the method comprising the steps of: a) culturing somato-sensory nerve cells ex vivo, b) loading the nerve cells with a calcium, sodium, or voltage-sensitive indicator or expressing a genetically encoded calcium, sodium, or voltage-sensitive indicator, c) pulsing the nerve cells with an electrical train of bipolar square waves at two different voltages and two different frequencies; wherein the first voltage is 10 V/cm or less (low voltage) and the second voltage is between 12 and 20 V/cm (high voltage); and wherein the first frequency is 5 Hz or less (low frequency) and the second frequency is between 15 and 20 Hz (high frequency), and d) detecting activation of the nerve cell by measuring the changes in the signal intensity of the indicator, wherein Aδ-type nerve cells are identified by low voltage and low frequency activation and a failure rate equal to or less than 50% at high voltage and high frequency, and wherein C-type nerve cells are identified by activation only at high voltage and a failure rate equal to or higher than 60% at high voltage and high frequency.

In another aspect, disclosed herein is a method of identifying a drug candidate selective for a Aδ-type nerve cell or a C-type nerve cell, the method comprising the steps of: a) culturing somato-sensory nerve cells ex vivo, b) loading the nerve cells with a calcium, sodium, or voltage-sensitive indicator or expressing a genetically encoded calcium, sodium, or voltage-sensitive indicator, c) pulsing the nerve cells with an electrical train of bipolar square waves at two different voltages and two different frequencies; wherein the first voltage is less than 10 V/cm (low voltage) and the second voltage is between 12 and 20 V/cm (high voltage); and wherein the first frequency is less than 5 Hz (low frequency) and the second frequency is between 15 and 20 Hz (high frequency), d) detecting activation of the nerve cell by measuring the changes in the signal intensity of the indicator, e) contacting an identified nerve cell with a drug candidate, and f) determining if the drug candidate selectively modulates the identified nerve cell, thereby identifying a drug candidate selective for a Aδ-type nerve cell or a C-type nerve cell, wherein Aδ-type nerve cells are identified by low voltage and low frequency activation and a failure rate equal to or less than 50% at high voltage and high frequency, and wherein C-type nerve cells are identified by activation only at high voltage and a failure rate equal to or higher than 60% at high voltage and high frequency.

In yet another aspect, disclosed herein is a method of providing a customized pain treatment for a patient in need thereof, the method comprising the steps of: a) culturing somato-sensory nerve cells from a patient ex vivo; wherein the patient has a known disease diagnosis, b) loading the nerve cells with a calcium, sodium, or voltage-sensitive indicator or expressing a genetically encoded calcium, sodium, or voltage-sensitive indicator, c) pulsing the nerve cells with an electrical train of bipolar square waves at two different voltages and two different frequencies; wherein the first voltage is 10 V/cm or less (low voltage) and the second voltage is between 12 and 20 V/cm (high voltage); and wherein the first frequency is 5 Hz or less (low frequency) and the second frequency is between 15 and 20 Hz (high frequency), d) detecting activation of the nerve cell by detecting the fluorescent dye, e) selecting a therapeutic drug to treat the patient based on the patient's diagnosis and the selectivity of the drug for either Aδ-type nerve cells or C-type nerve cells, thereby customizing the pain treatment for the patient, wherein low voltage and low frequency activation, or low voltage and high frequency activation indicates the nerve cell is a Aδ-type nerve cell, and wherein activation only detected at high voltage indicates the nerve cell is a C-type nerve cell. In some embodiments, the dye is a calcium sensitive dye.

In another aspect, disclosed herein is a method for assessing the potential efficacy of a selected drug for pain patient or a class of patients all exhibiting the same painful symptoms and pain type, the method comprising the steps of: a) measuring the drug's selectivity for Aδ or C fibers, or the lack of selectivity, based on the method disclosed herein; b) measuring, in a patient or a group of patients, the type of fiber damage employing one or more of the following methods: i) the Neurometer device, ii) quantitative sensory testing, iii) questionnaire-based nerve damage assessment; and c) establishing congruency between the drug selectivity, or lack thereof, for Aδ- and C-fibers and the type of damage observed in the patient, thereby assessing the efficacy of the drug.

DETAILED DESCRIPTION OF THE INVENTION

Figure 1:
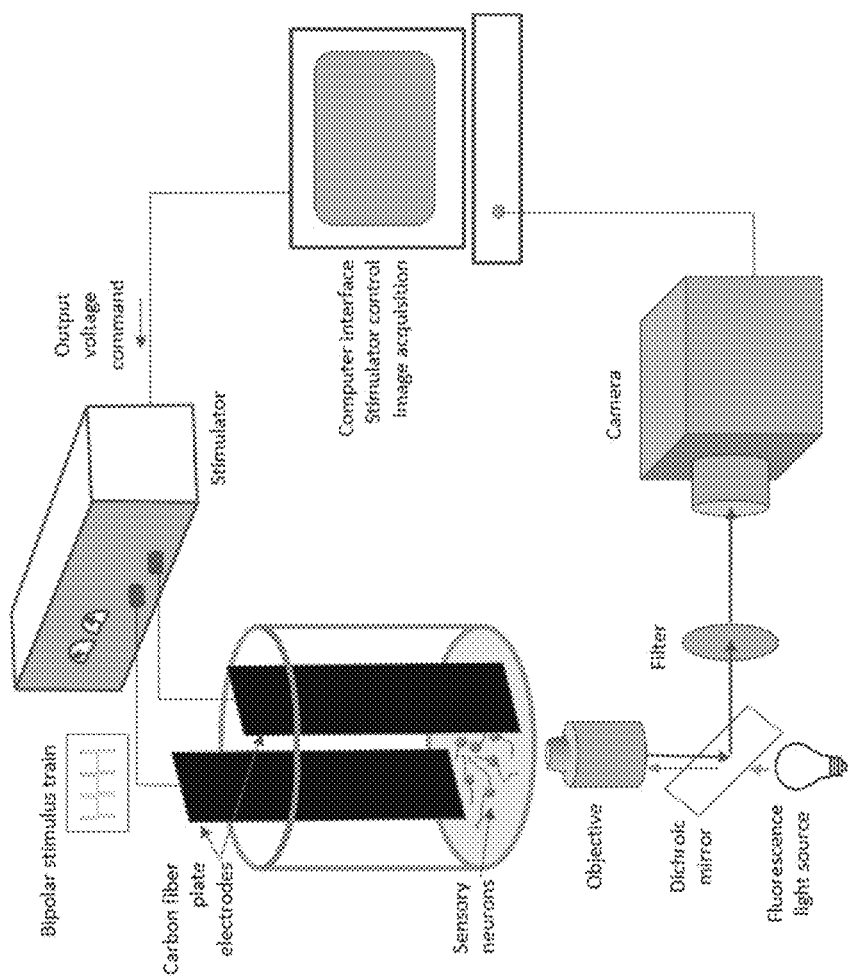
FIG. 1 illustrates the general layout of the experimental station 100 used in one preferred embodiment of the invention.

The present invention thus provides methods of distinguishing isolated Aδ-type nerve cells and C-type nerve cells in ex vivo cell culture. Once the nerve cells are identified, they can be used in a drug screening platform to identify old and new drugs that specifically modulate either Aδ-type nerve cells and C-type nerve cells, in particular human Aδ-type nerve cells and human C-type nerve cells. Classifying old and new drugs as either Aδ-type nerve cells or C-type nerve cells modulators will allow for more discriminating and sensitive pain therapy regimens. Furthermore, the methods can be used for paired diagnostic-therapeutic applications, using existing diagnostic methods combined with identification of a patient's Aδ-type nerve cells and C-type nerve cells and drugs that act specifically and selectively on the nerve cell associated with the diagnosis, thereby customizing therapeutic treatment for the patient.

Physiological pain is an important protective mechanism designed to warn of danger from potentially injurious stimuli from the external environment. The system operates through a specific set of primary sensory neurons and is activated by noxious stimuli via peripheral transducing mechanisms (see Millan, 1999, Prog. Neurobiol., 57, 1-164 for a review). These sensory fibers are known as nociceptors and are characteristically small diameter axons with slow conduction velocities. Nociceptors encode the intensity, duration and quality of noxious stimulus and, by virtue of their topographically organized projection to the spinal cord, the location of the stimulus. The nociceptors are found on nociceptive nerve fibers of which there are two main types, Aδ fibers (myelinated) and C fibers (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-teen pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitization in the periphery, locally around the injury and centrally where the nociceptors terminate. These effects lead to a heightened sensation of pain. In acute pain, these mechanisms can be useful in promoting protective behaviors which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibers associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli like allodynia— (Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibers. Myelinated Aδ fibers transmit rapidly and are responsible for sharp and stabbing pain sensations, whilst unmyelinated C fibers transmit at a slower rate and convey a dull or aching pain. Moderate to severe acute nociceptive pain is a prominent feature of pain from central nervous system trauma, strains/sprains, burns, myocardial infarction, and acute pancreatitis, post-operative pain (pain following any type of surgical procedure), posttraumatic pain, renal colic, cancer pain and back pain. Cancer pain may be chronic pain such as tumor related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally, but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple etiologies and thus can be classified in more than one area, e.g. back pain and cancer pain have both nociceptive and neuropathic components.

Other types of pain include: pain resulting from musculoskeletal disorders, including myalgia, fibromyalgia, spondylitis, sero-negative (non-rheumatoid) arthropathies, non-articular rheumatism, dystrophinopathy, glycogenolysis, polymyositis and pyomyositis; heart and vascular pain, including pain caused by angina, myocardial infarction, mitral stenosis, pericarditis, Raynaud's phenomenon, scleredoma and skeletal muscle ischemia; head pain, such as migraine (including migraine with aura and migraine without aura), cluster headache, tension-type headache mixed headache and headache associated with vascular disorders; and orofacial pain, including dental pain, otic pain, burning mouth syndrome and temporomandibular myofascial pain.

In one preferred embodiment of the invention, as illustrated in FIG. 1, human sensory neurons 109 are cultured under standard conditions and loaded with a calcium indicator to track their activation state. However, other kind of fluorescent indicators can be used, including voltage sensitive dyes and sodium indicators. A computer 101 controlled 102 stimulator 104 delivers trains of electrical impulses 111 to the chamber 110 containing the neurons 109, subjecting the cells to alternating electric field stimulations. The activation of the cells is then detected by recording the changes in fluorescent light emitted 113 by the calcium indicator, by means of a digital camera 105 connected 106 to the computer.

In order to differentiate between Aδ- and C-type cells the invention entails stimulating the cells at two different voltages and using trains delivered at two different frequencies. The clinical tools used to assess nerve fiber identity typically rely on the stimulation of >1 cm$^2$ of somatic surface, thereby recruiting bundles of sensory fibers. The individual fibers in a bundle subjected to very high frequency (≥200 Hz) stimulation are expected to experience a significant number of failures and only fire action potentials following a fraction of the stimuli in a high frequency train. However, given the large number of fibers, most stimuli will induce a response in at least some of the fibers and the overall response will follow the stimulus train and result in sensory perception. Given the shorter duration of action potentials in Aδ and Aδ fibers, compared to C-type, the former classes are expected to more effectively follow the high frequency stimulation.

When applying electrical stimulation strategies to classify individual isolated sensory neurons, the protocols used in the clinical setting are not effective. First, sine-wave stimulation results in the cells spending equal amount of time in a depolarized and in a hyperpolarized state during every stimulation cycle. This leads to numerous failures, due to the accumulation of inactivation of the voltage gated sodium channels expressed in the sensory neurons. Also, frequencies >20 Hz result in large number of action potential failures as the inter-pulse interval is shorter that the time constant of recovery from inactivation for many of the voltage gated sodium channels. This means that the stimulation protocols used in the clinical setting, would not work in an ex vivo preparation in which it is important to identify and categorize the response of every individual cell in the dish.

Figure 2:
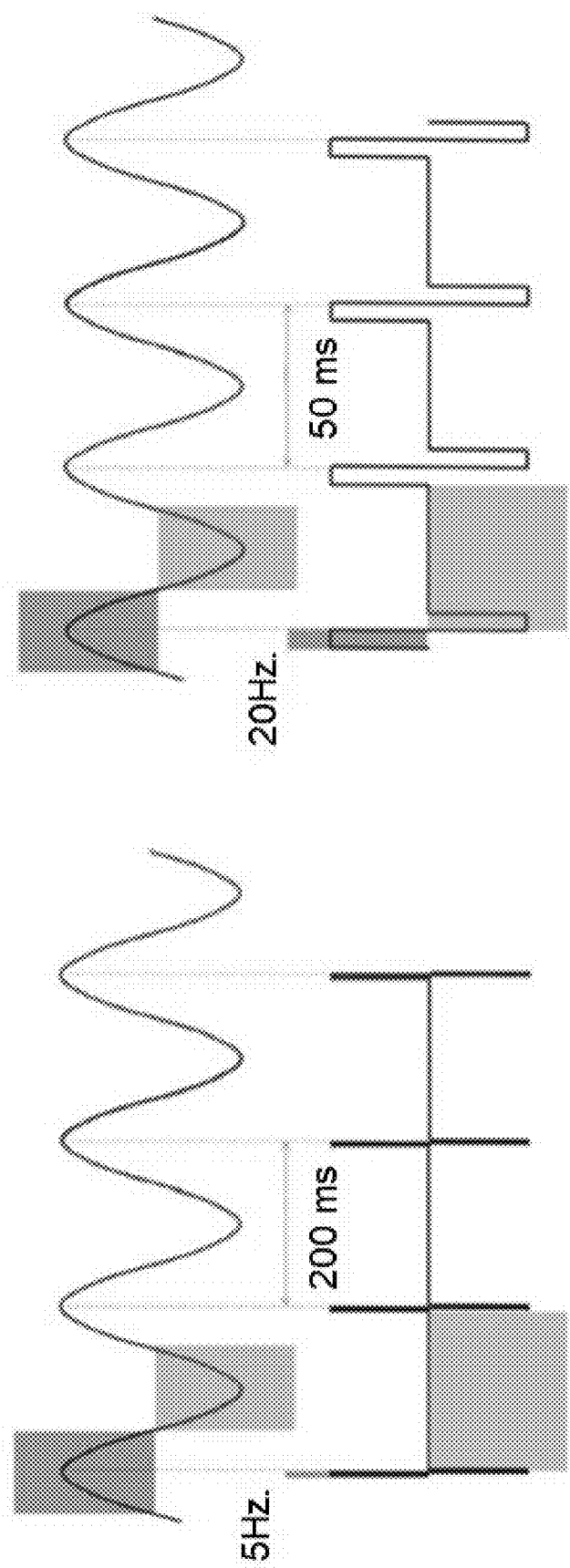
FIG. 2 illustrates an advantage intrinsic to the bipolar square pulses used in the present invention, compared to sine-waves.

FIG. 2 illustrates a critical advantage intrinsic to the bipolar square pulses used in the present invention, compared to sine-waves (compare, e.g., Koga et al., Molecular Pain 1:13 (2005)). By virtue of the inter-pulse interval and the opposite polarity of the two square waves delivered at each pulse, the cells can spend most of the time in the hyperpolarized and in the resting state, during which the sodium channels have time to recover from inactivation. This results in a low failure rate: most stimuli can elicit a response in each one of the cells being analyzed. Therefore, the use of a train of bipolar square pulses in the present invention is critical for the successful categorization of each individual cell.

In a preferred embodiment of this invention, two sets of train stimulations are delivered at frequencies <20 Hz. Preferably, one train is delivered at frequencies ≤5 Hz, while the second train is delivered at a frequency ≥15 Hz and ≤20 Hz. Cells are also tested by delivering a high and a low voltage field stimulation. Therefore, a 2×2 matrix of stimulation conditions is to be used in a preferred embodiment of the present invention in which two voltage field intensities and two stimulation frequencies are employed. A typical low voltage field stimulation is delivered at ≤10 V/cm while the high voltage stimulation is delivered at 12≤V/cm≤20.

Table 1 summarizes the matrix of stimulation conditions and the assignment of each cell to either one of the two classes based on the response failure rates. Using the methodologies described in the present invention it is possible to classify Aδ cells as cells that respond at low voltage; in addition, Aδ cells, when stimulated at high voltage exhibit failure rates ≤50% at low frequency and ≤75% and high frequency stimulation. C-type cells do not respond at low voltage intensity stimulation, and exhibit failure rates ≥60% at high voltage/high frequency stimulation. When stimulated at high voltage and low frequency, both type of cells exhibit similar responses and therefore this stimulation condition is not able to discriminate the two cell classes. As apparent from Table 1, the present invention enables the identification of different classes of sensory neurons even based on a single run. Low voltage/low frequency, or low voltage/high frequency, or high voltage/high frequency, can each, discriminate between cells of the Aδ- and C class. However, in a preferred embodiment of the present invention, the three conditions listed above are all used and the results are combined to achieve a higher degree of confidence in the final classification.

TABLE 1

| | Aδ-type cells; C type cells | |
|---|---|---|
| Failure rate (Cell Class) | Low Frequency (≤5 Hz) | High Frequency (15 ≤ Hz ≤ 20) |
| Low Voltage (≤10 V/cm) | ≤50% (Aδ) No response (C) | ≤75% (A Aδ) No response (C) |
| High Voltage (12 ≤ V/cm ≤ 20) | ≤50% ≤50% | ≤50% (A Aδ) ≥60% (C) |

The methods of the invention are used to identify either Aδ-type nerve cells or C-type nerve cells. In some cases, various pain conditions are known to be modulated specifically by one or the other of these cell types. Therefore, identification of old or new therapeutic compounds that specifically modulate either Aδ-type nerve cells or C-type nerve cells is essential for specifically treating such disease states. The methods of the invention are used for drug discovery and also for paired diagnostic-therapeutics. Once a disease state is identified using conventional diagnostic tools, the methods of the invention can be used to identify the nerve cell type affected by the disease, and the appropriate therapeutic drug can be matched to the affected nerve cell type.

Exemplary conditions that can be treated using the compounds identified using the methods described herein include pain. The term "pain" refers to all categories of pain, including pain that is described in terms of stimulus or nerve response, e.g., somatic pain (normal nerve response to a noxious stimulus) and neuropathic pain (abnormal response of an injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, AIDS pain, arthropathy, migraine, trigeminal neuralgia, cardiac ischaemia, and diabetic neuropathy (see, e.g., Harrison's Principles of Internal Medicine, pp. 93-98 (Wilson et al., eds., 12th ed. 1991); Williams et al., J. of Med. Chem. 42: 1481-1485 (1999), herein each incorporated by reference in their entirety).

"Somatic" pain, as described above, refers to a normal nerve response to a noxious stimulus such as injury or illness, e.g., trauma, burn, infection, inflammation, or disease process such as cancer, and includes both cutaneous pain (e.g., skin, muscle or joint derived) and visceral pain (e.g., organ derived).

"Neuropathic" pain, as described above, refers to pain resulting from injury to or chronic changes in peripheral and/or central sensory pathways, where the pain often occurs or persists without an obvious noxious input.

"Acute pain", as described above, refers to pain which is marked by short duration or a sudden onset.

"Chronic pain", as described above, refers to pain which is marked by long duration or frequent recurrence.

"Inflammatory pain", as described above, refers to pain which is produced as a symptom or a result of inflammation or an immune system disorder.

"Visceral pain", as described above, refers to pain which is located in an internal organ.

Acute pain as used herein includes but is not limited to nociceptive pain and post-operative pain. Chronic pain includes but is not limited by: peripheral neuropathic pain (e.g., post-herpetic neuralgia, diabetic neuropathic pain, neuropathic cancer pain, HIV-associated neuropathy, erythromelalgia, failed back-surgery syndrome, trigeminal neuralgia, or phantom limb pain); central neuropathic pain (e.g., multiple sclerosis related pain, Parkinson disease related pain, post-stroke pain, post-traumatic spinal cord injury pain, lumbosacral radiculopathy, cervical radiculopathy, brachial radiculopathy, or pain in dementia); musculoskeletal pain such as osteoarthritic pain and fibromyalgia syndrome; inflammatory pain (e.g., inflammatory pain caused by rheumatoid arthritis, juvenile idiopathic arthritis, ankylosing spondylitis, psoriatic arthritis, inflammatory bowel disease, primary dysmenorrhea, or endometriosis); headache such as migraine, cluster headache, tension headache syndrome, facial pain, headache caused by other diseases; visceral pain such as interstitial cystitis, irritable bowel syndrome and chronic pelvic pain syndrome; and mixed pain such as lower back pain, neck and shoulder pain, burning mouth syndrome and complex regional pain syndrome.

Methods of culturing isolated neurons in vitro or ex vivo are well known in the art (see, e.g., Neuronal Cell Culture: Methods and Protocols 2013 (Amini & White, eds.)). Typically, human neurons are used in the methods of the invention, although neurons from other standard experimental animals such as rats, mice and non-human primates can also be used. In one embodiment, the neurons are from immortalized cell lines. Typically, the neurons are primary neuronal cultures. The primary nerve cultures can be from any suitable source, such as rodents, non-human primates or human organ/tissue donors.

The activity of a Aδ-type nerve cell or C-type nerve cell in response to a drug candidate can be assessed using a variety of in vitro assays, including but not limited to, measuring ion flux, measuring transmembrane potential, and/or measuring ionic current. Measurement of ionic fluxes can be accomplished by measuring changes in the concentration of the permeant species or by tracking the movement of small amounts of an appropriately permeant radioactive or fluorescent tracer. Activation and transmembrane potential can be assessed with calcium sensitive fluorescent dyes, sodium sensitive fluorescent dyes, voltage-sensitive fluorescent dyes, genetically encoded indicators of membrane potential or genetically encoded indicators of intracellular ions.

Changes in ion flux may be assessed by determining changes in polarization (i.e., electrical potential) of the cell. A preferred means to determine changes in cellular polarization is by measuring changes in current or voltage with the voltage-clamp and patch-clamp techniques, using the "cell-attached" mode, the "inside-out" mode, the "outside-out" mode, the "perforated patch" mode, the "whole cell" mode or other means of controlling or measuring changes in transmembrane potential (see, e.g., Ackerman et al., New Engl. J. Med., 336: 1575-1595 (1997)). Whole cell currents are conveniently determined using the standard methodology (see, e.g., Hamill et al., Pflugers. Archiv. 391: 85 (1981). Other known assays include: radiotracer flux assays and fluorescence assays using voltage-sensitive dyes (see, e.g., Vestergarrd-Bogind et al., J. Membrane Biol. 88: 67-75 (1988); Daniel et al., J. Pharmacol. Meth. 25: 185-193 (1991); Holevinsky et al., J. Membrane Biology 137: 59-70 (1994)). Assays for compounds capable of modulating activity of the nerve cell can be performed by application of the compounds to a bath solution in contact with and comprising the (see, e.g., Blatz et al., Nature 323: 718-720 (1986); Park, J. Physiol. 481: 555-570 (1994)). Generally, the compounds to be tested are present in the range from about 1 nM to about 100 mM.

The effects of the test compounds upon the function of the cells can be measured by changes in the electrical currents or ionic flux or by the consequences of changes in currents and flux. Changes in electrical current or ionic flux are measured by either increases or decreases in flux of ions such as sodium or guanidinium ions (see U.S. Pat. No. 5,688,830). The cations can be measured in a variety of standard ways. They can be measured directly by concentration changes of the ions or indirectly by membrane potential or by using radioactive ions. Consequences of the test compound on ion flux can be quite varied. Accordingly, any suitable physiological change can be used to assess the influence of a test compound on the cells of this invention. When the functional consequences are determined, one can also measure a variety of effects such as transmitter release, hormone release, transcriptional changes to both known and uncharacterized genetic markers, changes in cell metabolism such as cell growth or pH changes, and changes in intracellular second messengers such as $Ca^{2+}$, or cyclic nucleotides. High throughput screening (HTS) is of use in identifying promising new drugs using the methods of the invention.

Modulation of a nerve cell can be tested using one of the in vitro or in vivo assays described above. Samples or assays that are treated with a potential drug are compared to control samples without the test compound, to examine the extent of modulation. Control samples (untreated with inhibitors) are assigned a relative activity value of 100. Inhibition is achieved when the sodium channel value relative to the control is less than 70%, preferably less than 40% and still more preferably, less than 30%.

As described above, calcium, sodium and voltage sensitive fluorescent dyes can be used to determine when the nerve cell is activated using the methods of the invention. Images of activated cells are taken using standard imaging techniques. FIG. 1 shows a typical system 100 of the invention. The cultured neurons 109 are in a dish 110 with electrodes 112, which transmit the bipolar stimulus train 111. A microscope 107 connected to a camera 105, mirror 114, filter 115, and a fluorescent light source 108 takes images of the neurons 109, which are transmitted to the computer interface 101, which also controls the electrical stimulator 104 and regulates the voltage and frequency 103 of the electrical current.

Chemical calcium indicators are small molecules that can chelate calcium ions, and are linked to fluorescent reporters. These molecules are based on an EGTA homologue called BAPTA, with high selectivity for calcium ($Ca^{2+}$) ions versus magnesium ($Mg^{2+}$) ions. This group of indicators includes fura-2, indo-1, fluo-3, fluo-4, and Calcium Green-1. These dyes are often used with the chelator carboxyl groups masked as acetoxymethyl esters, in order to render the molecule lipophilic and to allow easy entrance into the cell. Once this form of the indicator is in the cell, cellular esterases will free the carboxyl groups and the indicator will be able to bind calcium. The free acid form of the dyes (i.e., without the acetoxymethyl ester modification) can also be directly injected into cells via a microelectrode or micropipette which removes uncertainties as to the cellular compartment holding the dye for example the acetoxymethyl ester can also enter the endoplasmic reticulum and mitochondria. Binding of a $Ca^{2+}$ ion to a fluorescent indicator molecule leads to either an increase in quantum yield of fluorescence or emission/excitation wavelength shift.

Voltage-sensitive dyes, also known as potentiometric dyes, are dyes which change their spectral properties in response to voltage changes. They are able to provide linear measurements of firing activity of single neurons or large neuronal populations. Both fast and slow response dyes are available.

Fast-response probes: These are amphiphilic membrane staining dyes which usually have a pair of hydrocarbon chains acting as membrane anchors and a hydrophilic group which aligns the chromophore perpendicular to the membrane/aqueous interface. The chromophore is believed to undergo a large electronic charge shift as a result of excitation from the ground to the excited state and this underlies the putative electrochromic mechanism for the sensitivity of these dyes to membrane potential. This molecule (dye) intercalates among the lipophilic part of biological membranes. This orientation assures that the excitation induced charge redistribution will occur parallel to the electric field within the membrane. A change in the voltage across the membrane will therefore cause a spectral shift resulting from a direct interaction between the field and the ground and excited state dipole moments. New voltage dyes can sense voltage with high speed and sensitivity using photoinduced electron transfer (PeT) through a conjugated molecular wire.

Slow-response probes: These exhibit potential-dependent changes in their transmembrane distribution which are accompanied by a fluorescence change. Typical slow-response probes include cationic carbocyanines and rhodamines, and ionic oxonols.

Examples of sodium molecular sensors include crown ethers with large affinity for sodium ions but not for potassium and forms of metal detection by so-called complexones which are traditional pH indicators retrofitted with molecular groups sensitive to metals. This receptor-spacer-reporter concept is a recurring theme often with the reporter displaying photoinduced electron transfer (PET). The sensor is linked to a fluorescent reporter molecule such rhodamine.

Standard organic fluorophores belong to following major chemical families:
Xanthene derivatives: fluorescein, rhodamine, Oregon green, eosin, and Texas red.
Cyanine derivatives: cyanine, indocarbocyanine, oxacarbocyanine, thiacarbocyanine, and merocyanine.
Squaraine derivatives and ring-substituted squaraines, including Seta, SeTau, and Square dyes Naphthalene derivatives (dansyl and prodan derivatives).
Coumarin derivatives.
Oxadiazole derivatives: pyridyloxazole, nitrobenzoxadiazole and benzoxadiazole.
Anthracene derivatives: anthraquinones, including DRAQ5, DRAQ7 and CyTRAK Orange.
Pyrene derivatives: cascade blue, etc.
Oxazine derivatives: Nile red, Nile blue, cresyl violet, oxazine 170, etc.
Acridine derivatives: proflavin, acridine orange, acridine yellow, etc.
Arylmethine derivatives: auramine, crystal violet, malachite green
Tetrapyrrole derivatives: porphin, phthalocyanine, bilirubin.

Pain medications are drugs used to relieve discomfort associated with disease, injury, or surgery. Because the pain process is complex, there are many types of pain drugs that provide relief by acting through a variety of physiological mechanisms. Thus, effective medication for nerve pain will likely have a different mechanism of action than arthritis pain medication. The present invention provides methods for distinguishing the action of drugs on different sensory nerve fibers. The following list represents certain classes of pain medications:

Nonsteroidal anti-inflammatory drugs (NSAIDs) act on substances in the body that can cause inflammation, pain, and fever. Common NSAIDs include aspirin, ibuprofen, ketoprofen, naproxen, diclofenac, and ketorolac. COX-2 inhibitors (coxibs) are a relatively new type of prescription NSAIDs that reduces pain and inflammation by blocking a specific enzyme (COX-2) in the body. These medications target only the COX-2 enzyme that stimulates the inflammatory response. Currently, only celecoxib (CELEBREX™) remains on the market.

Corticosteroids are often administered as an injection at the site of musculoskeletal injuries. They exert powerful anti-inflammatory effects. They can also be taken orally to relieve pain from, for example, arthritis. Common classes of corticosteroids include progesterone-type, hydrocortisone-type, methasone-type and acetonides.

Acetaminophen (TYLENOL™) increases the body's pain threshold, but it has little effect on inflammation.

Opioids, also known as narcotic analgesics, modify pain messages in the brain. Common synthetic, semi-synthetic and natural opioids include codeine (TYLENOL 3™), propoxyphene (DARVOCET™), hydrocodone (VICODIN™), oxycodone (PERCOCET™, OXYCONTIN™). The most potent opioids are fentanyl (SUBLIMAZE™), hydromorphone (DILAUDID™), meperidine (DEMEROL™), and morphine, oxymorphone (NUMORPHAN™).

Muscle relaxants reduce pain from tense muscle groups, most likely through sedative action in the central nervous system. The term "muscle relaxant" is used to refer to two major therapeutic groups: neuromuscular blockers and spasmolytics. Common muscle relaxants include dantrolene, baclofen, clonidine and other imidazolines, methocarbamol, carisoprodol, chlorzoxazone, cyclobenzaprine, gabapentin, metaxalone, and orphenadrine.

Anti-anxiety drugs work on pain in three ways: they reduce anxiety, they relax muscles, and they help patients cope with discomfort. Common benzodiazepines include XANAX™ (alprazolam), KLONOPIN™ (clonazepam), VALIUM™ (diazepam), and ATIVAN™ (lorazepam).

Some antidepressants, particularly the tricyclics, may reduce pain transmission through the spinal cord. Common tricyclics include amitriptyline, nortriptyline and desipramine.

Some anti-epileptic drugs also relieve the pain of neuropathies, possibly by stabilizing nerve cells. Common anti-epileptic drugs include gabapentin (NEUROTIN™), pregabalin, phenytoin, carbamazepine, valproic acid, lamotrigine, topiramate, and oxcarbazepine.

Each of these classes of drugs may be tested using the methods of the invention, to determine their selectivity and specificity for Aδ-type nerve cells or C-type nerve cells. Knowledge of the type of nerve cell modulated by a drug, coupled with a known disease diagnosis, allows customized pain treatment. In addition to know classes of drugs, new drugs can be screened using the methods of the invention, e.g., using high throughput screening methods.

EXAMPLES

Methods
Human DRG Neurons Isolation and Culture:
DRGs from the first thoracic vertebra (T1) through the first sacral vertebra (S1) were used in the present study. Human DRG neurons where isolated from organ donors for which full legal and ethical consent had been obtained. The DRGs were stripped of connective tissue and enzymatically digested at 37° C. for 2 h using AnaBios' proprietary enzyme mixture. Samples were then centrifuged for 2 min at 200×g, supernatant was gently removed, and tissue was washed 4 times, followed by resuspension in DMEM/F12 (Lonza) containing 1% horse serum (Thermo Fisher Scientific). Ganglia were mechanically dissociated by gentle trituration through the fire-polished tip of a sterile glass Pasteur pipette. Dissociated cells were seeded on glass coverslips that had been pre-coated with poly-D-lysine (Corning) for electrophysiology experiments or in 96-well plastic bottom plates (Corning) that had been pre-coated with ply-D-lysine. Cells were maintained in culture at 37° C. with 5% CO2 in DMEM/F12 supplemented with 10% horse serum (Thermo Fisher Scientific), 2 mM glutamine, 25 ng/mL hNGF (Cell Signaling Technology, Danvers, Mass.), 25 ng/mL GDNF (Peprotech), and penicillin/streptomycin (Thermo Fisher Scientific). Half of the culture media was replaced with fresh media every 3 days.

Live Cell Calcium Imaging:

Cells were loaded with 3 M Fluo-8-AM (AAT Bioquest) containing 0.1% Pluronic F-127 (Sigma) for 20 min. at room temperature. Extracellular solution contained in (mM): 145 NaCl, 3 KCl, 2 CaCl2), 1 MgCl2, 10 HEPES, 10 glucose adjusted to pH 7.4 with NaOH. Fluo-8-loaded cells were excited at 480 nm and emission was collected at 520 nm with a pcoEDGE sCMOS camera (PCO) mounted on an inverted microscope (Olympus IX71).

For Electric Field stimulation (EFS), images were acquired at 100 Hz while simultaneously applying a train of 10 or 20 pulses bipolar, each with a duration of 10 ms at a frequency of 5 or 20 Hz using a Master 8 electronic stimulator (AMPI). Stimulus intensity was set at 7.5V/cm (low voltage) or 15V/cm (high voltage). The two different intensities were set after determining that in our experimental chamber the low voltage stimulation was at threshold for generating responses from a subset of cells, while the high voltage consistently provided supra-threshold stimulation with the maximal response to EFS that still exhibited sensitivity to lidocaine (200 μA). A 2 minute resting interval was observed between trains of EFS when EFS was repeated multiple times.

Results

Figure 3:
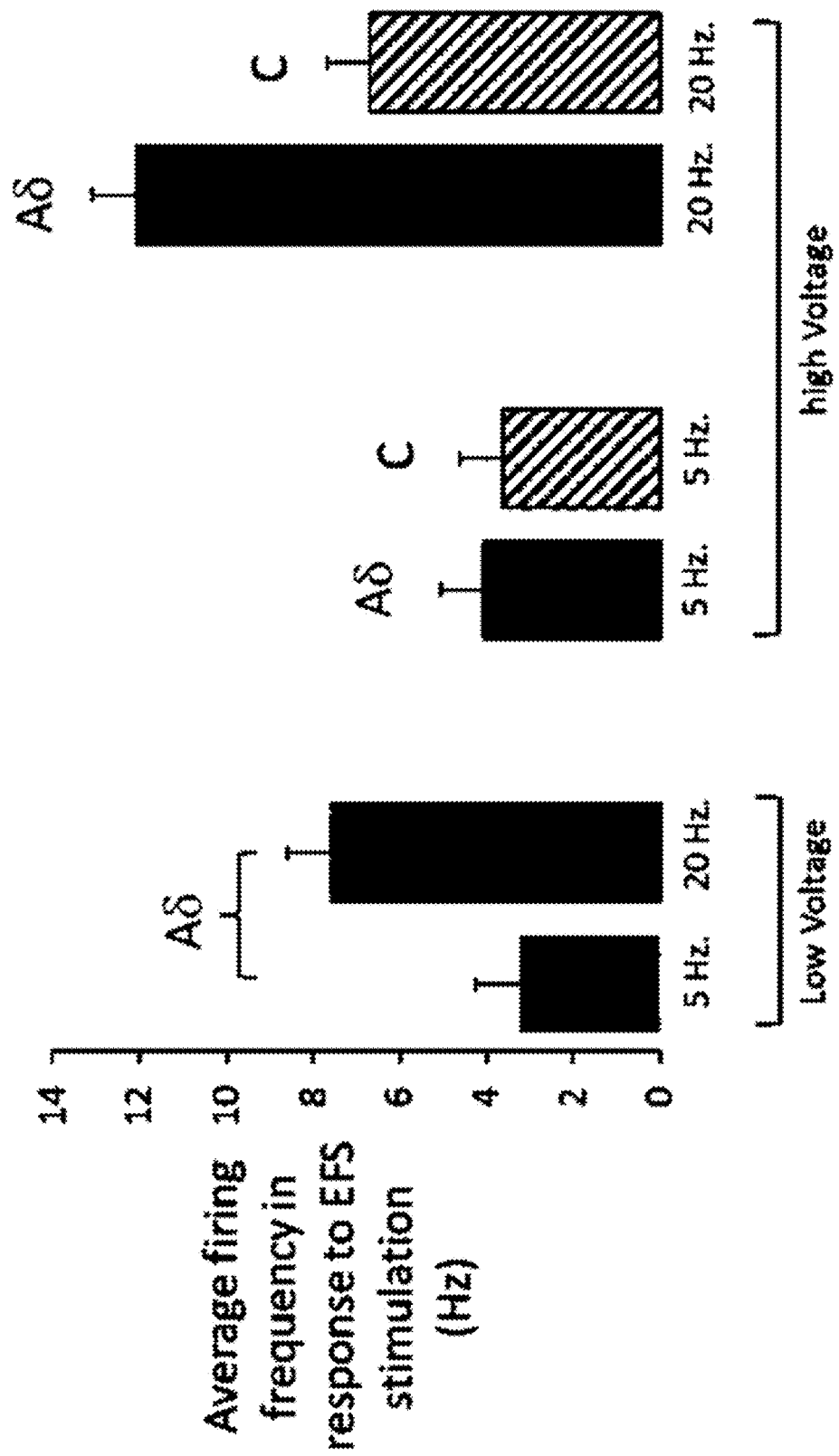
FIG. 3 shows identification of Aδ- and C-like neurons based on EFS responses.

FIG. 3 shows human DRG neurons (n=134 from 2 donors) were stimulated with EFS trains delivered sequentially at different frequencies (5 and 20 Hz) and 2 different voltage intensities (low voltage: 7.5V/cm; high voltage 15V/cm). For each cell, the firing frequency was obtained by counting the number of spikes in the calcium transients and applying the algorithm described in the methods section. Solid bars indicate Aδ-like cells; hashed bars indicate C-like cells.

Figure 4:
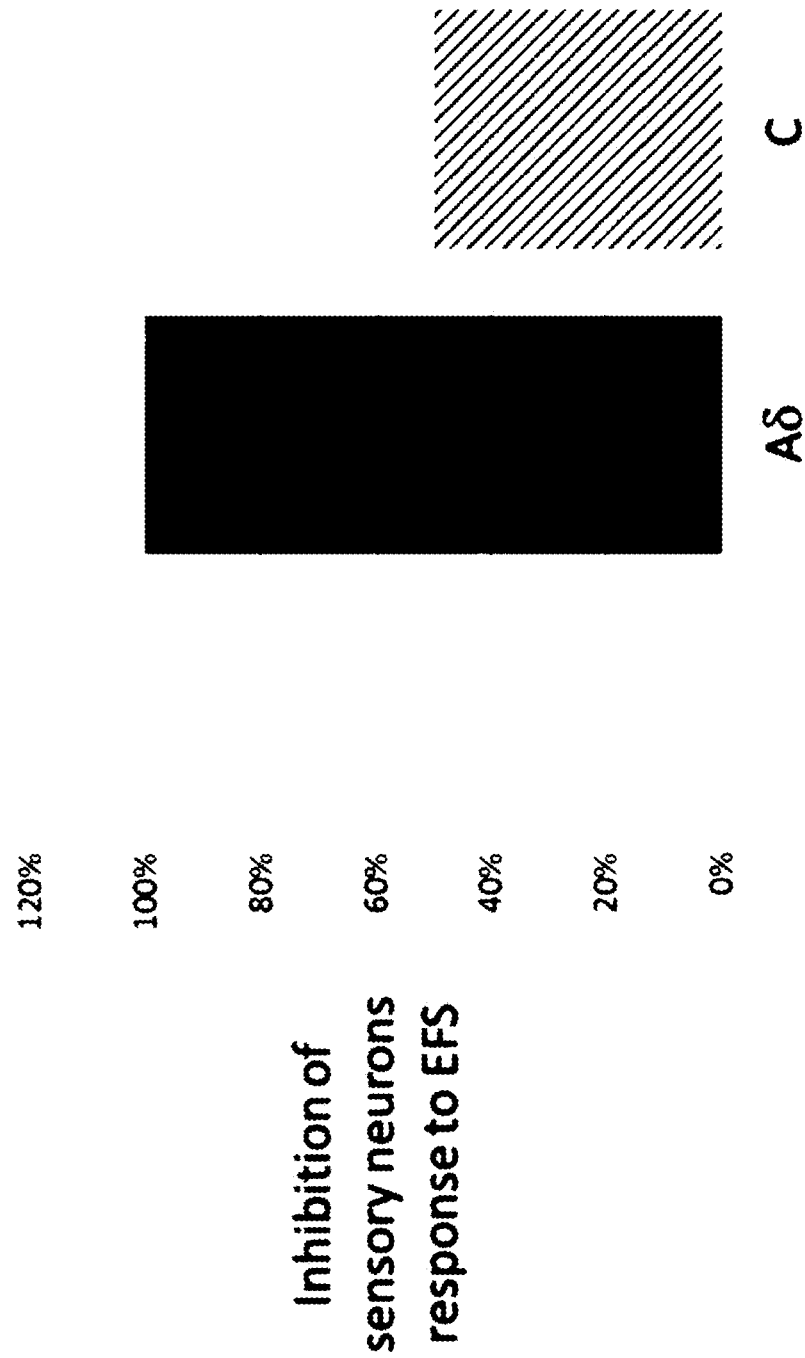
FIG. 4 shows the differential effect of Drug A on Aδ- and C-type neurons.
Figure 5:
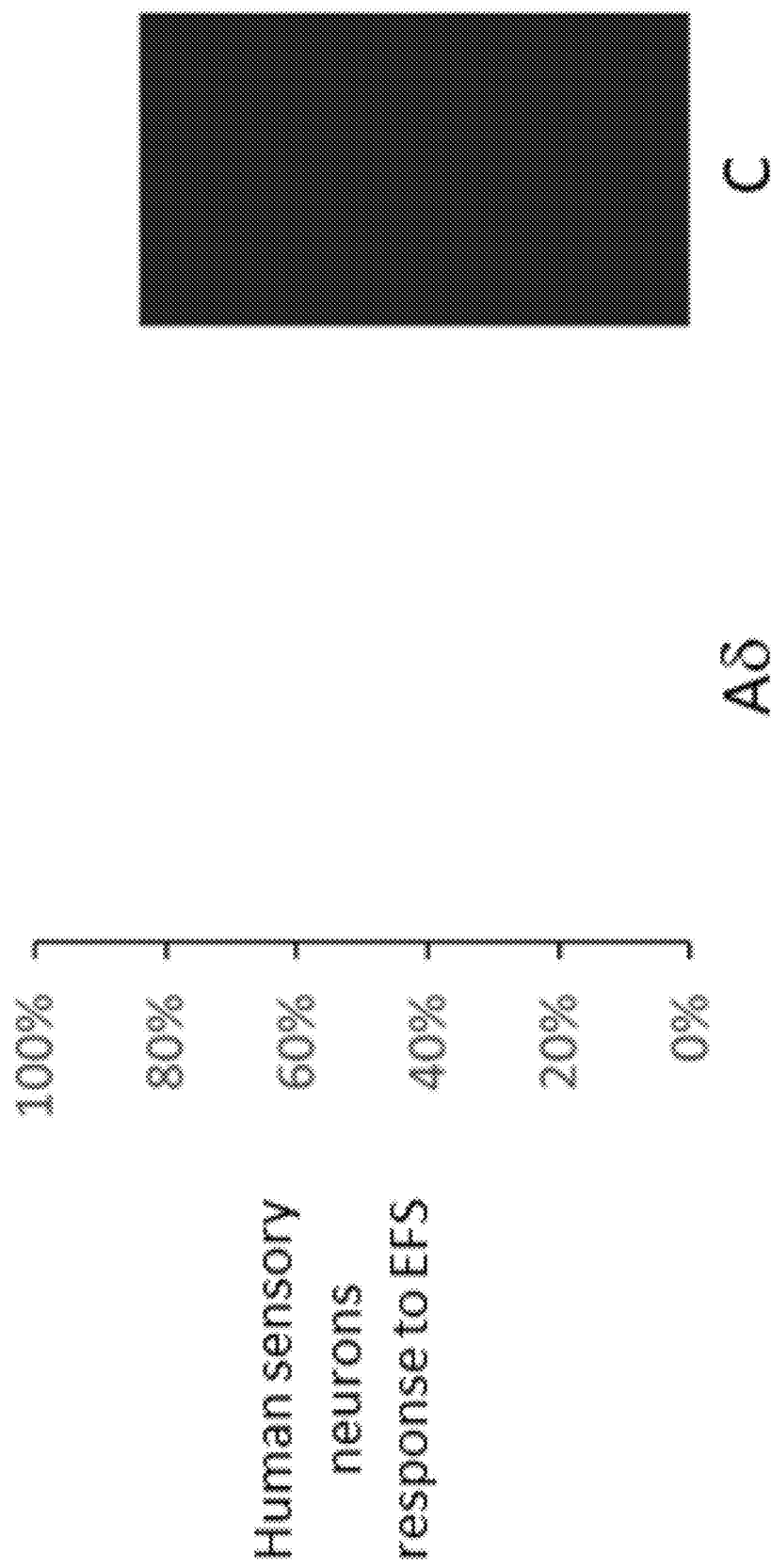
FIG. 5 shows the differential effect of Drug B on Aδ- and C-type neurons.

FIG. 4 shows the activity of sensory neurons in response to EFS in the presence of Drug A (and measured relative to the response in control, buffer) is shown. Drug A appears to preferentially block C-type cells. FIG. 5 shows the activity of sensory neurons in response to EFS in the presence of Drug B (and measured relative to the response in control, buffer) is shown. Drug B appears to preferentially block C-type cells.

Traditionally, the distinction between Aδ and C-fibers has relied mostly on the different conduction velocity between the two fibers, which is ultimately a result of the myelination of the Aδ fibers. However, the two fiber types also exhibit divergent patterns of expression of a number of voltage gated ion channels which enable Aδ- and C-type nociceptors to respond distinctly to patterned electrical stimulation. This feature is employed in the clinics in the use of the Neurometer device and has been leverage by the present invention. The preservation of the naïve expression patterns of voltage gated channels in in vitro cell culture systems, has allowed us to develop electrical stimulation paradigms that distinguish the two fiber types.

In one aspect, disclosed herein is a method of identifying and distinguishing different types of nerve cells in ex vivo cell culture, the method comprising the steps of: a) culturing somato-sensory nerve cells ex vivo, b) loading the nerve cells with a calcium, sodium, or voltage-sensitive indicator or expressing a genetically encoded calcium, sodium, or voltage-sensitive indicator, c) pulsing the nerve cells with an electrical train of bipolar square waves at two different voltages and two different frequencies; wherein the first voltage is 10 V/cm or less (low voltage) and the second voltage is between 12 and 20 V/cm (high voltage); and wherein the first frequency is 5 Hz or less (low frequency) and the second frequency is between 15 and 20 Hz (high frequency), and d) detecting activation of the nerve cell by measuring the changes in the signal intensity of the indicator, wherein low voltage and low frequency activation indicates a first type of cell and activation detected only at high voltage indicates a second type of cell.

In some embodiments, the nerve cell is a human nerve cell, a rodent nerve cells or a non-human primate nerve cell.

In some embodiments, wherein the indicator is a calcium sensitive indicator.

In another aspect, disclosed herein is a method of identifying and distinguishing Aδ-type nerve cells and C-type nerve cells in ex vivo cell culture, the method comprising the steps of: a) culturing somato-sensory nerve cells ex vivo, b) loading the nerve cells with a calcium, sodium, or voltage-sensitive indicator or expressing a genetically encoded calcium, sodium, or voltage-sensitive indicator, c) pulsing the nerve cells with an electrical train of bipolar square waves at two different voltages and two different frequencies; wherein the first voltage is 10 V/cm or less (low voltage) and the second voltage is between 12 and 20 V/cm (high voltage); and wherein the first frequency is 5 Hz or less (low frequency) and the second frequency is between 15 and 20 Hz (high frequency), and d) detecting activation of the nerve cell by measuring the changes in the signal intensity of the indicator, wherein low voltage and low frequency activation, or low voltage and high frequency activation indicates the nerve cell is a Aδ-type nerve cells and activation detected only at high voltage indicates the nerve cell is a C-type nerve cell.

In some embodiments, the nerve cell is a human nerve cell, a rodent nerve cells or a non-human primate nerve cell.

In some embodiments, the indicator is a calcium sensitive indicator.

In yet another aspect, disclosed herein is a method of identifying a drug candidate selective for a Aδ-type nerve cell or a C-type nerve cell, the method comprising the steps of: a) culturing somato-sensory nerve cells ex vivo, b) loading the nerve cells with a calcium, sodium, or voltage-sensitive indicator or expressing a genetically encoded calcium, sodium, or voltage-sensitive indicator, c) pulsing the nerve cells with an electrical train of bipolar square waves at two different voltages and two different frequencies; wherein the first voltage is less than 10 V/cm (low voltage) and the second voltage is between 12 and 20 V/cm (high voltage); and wherein the first frequency is less than 5 Hz (low frequency) and the second frequency is between 15 and 20 Hz (high frequency), d) detecting activation of the nerve cell by measuring the changes in the signal intensity of the indicator, e) contacting an identified nerve cell with a drug candidate, and f) determining if the drug candidate selectively modulates the identified nerve cell, thereby identifying a drug candidate selective for a Aδ-type nerve cell or a C-type nerve cell, wherein low voltage and low frequency activation, or low voltage and high frequency activation indicates the nerve cell is a Aδ-type nerve cells and activation detected only at high voltage indicates the nerve cell is a C-type nerve cell.

In some embodiments, the drug candidate is selected from the group consisting of NSAID, corticosteroid, acetaminophen, opioid, muscle relaxant, anti-anxiety, tricyclic antidepressant, a local anesthetic, a voltage gated channel inhibitor, and anti-epileptic.

In some embodiments, the drug candidate has not previously been used to treat pain.

In some embodiments, the nerve cell is a human nerve cell, a rodent nerve cell, or a non-human primate nerve cell.

In some embodiments, the indicator is a calcium sensitive indicator.

In another aspect, disclosed herein is a method of identifying and distinguishing Aδ-type nerve cells and C-type nerve cells in ex vivo cell culture, the method comprising the steps of: a) culturing somato-sensory nerve cells ex vivo, b) loading the nerve cells with a calcium, sodium, or voltage-sensitive indicator or expressing a genetically encoded calcium, sodium, or voltage-sensitive indicator, c) pulsing the nerve cells with an electrical train of bipolar square waves at two different voltages and two different frequencies; wherein the first voltage is 10 V/cm or less (low voltage) and the second voltage is between 12 and 20 V/cm (high voltage); and wherein the first frequency is 5 Hz or less (low frequency) and the second frequency is between 15 and 20 Hz (high frequency), and d) detecting activation of the nerve cell by measuring the changes in the signal intensity of the indicator, wherein Aδ-type nerve cells are identified by low voltage and low frequency activation and a failure rate equal to or less than 50% at high voltage and high frequency, and wherein C-type nerve cells are identified by activation only at high voltage and a failure rate equal to or higher than 60% at high voltage and high frequency.

In some embodiments, the drug candidate is selected from the group consisting of NSAID, corticosteroid, acetaminophen, opioid, muscle relaxant, anti-anxiety, tricyclic antidepressant, a local anesthetic, a voltage gated channel inhibitor, and anti-epileptic.

In some embodiments, the drug candidate has not previously been used to treat pain.

In some embodiments, the nerve cell is a human nerve cell, a rodent nerve cell, or a non-human primate nerve cell.

In some embodiments, the indicator is a calcium sensitive indicator.

In another aspect, disclosed herein is a method of identifying a drug candidate selective for a Aδ-type nerve cell or a C-type nerve cell, the method comprising the steps of: a) culturing somato-sensory nerve cells ex vivo, b) loading the nerve cells with a calcium, sodium, or voltage-sensitive indicator or expressing a genetically encoded calcium, sodium, or voltage-sensitive indicator, c) pulsing the nerve cells with an electrical train of bipolar square waves at two different voltages and two different frequencies; wherein the first voltage is less than 10 V/cm (low voltage) and the second voltage is between 12 and 20 V/cm (high voltage); and wherein the first frequency is less than 5 Hz (low frequency) and the second frequency is between 15 and 20 Hz (high frequency), d) detecting activation of the nerve cell by measuring the changes in the signal intensity of the indicator, e) contacting an identified nerve cell with a drug candidate, and f) determining if the drug candidate selectively modulates the identified nerve cell, thereby identifying a drug candidate selective for a Aδ-type nerve cell or a C-type nerve cell, wherein Aδ-type nerve cells are identified by low voltage and low frequency activation and a failure rate equal to or less than 50% at high voltage and high frequency, and wherein C-type nerve cells are identified by activation only at high voltage and a failure rate equal to or higher than 60% at high voltage and high frequency.

In some embodiments, the drug candidate is selected from the group consisting of NSAID, corticosteroid, acetaminophen, opioid, muscle relaxant, anti-anxiety, tricyclic antidepressant, a local anesthetic, a voltage gated channel inhibitor, and anti-epileptic.

In some embodiments, the drug candidate has not previously been used to treat pain.

In some embodiments, the nerve cell is a human nerve cell, a rodent nerve cell, or a non-human primate nerve cell.

In some embodiments, the indicator is a calcium sensitive indicator.

In yet another aspect, disclosed herein is a method of providing a customized pain treatment for a patient in need thereof, the method comprising the steps of: a) culturing somato-sensory nerve cells from a patient ex vivo; wherein the patient has a known disease diagnosis, b) loading the nerve cells with a calcium, sodium, or voltage-sensitive indicator or expressing a genetically encoded calcium, sodium, or voltage-sensitive indicator, c) pulsing the nerve cells with an electrical train of bipolar square waves at two different voltages and two different frequencies; wherein the first voltage is 10 V/cm or less (low voltage) and the second voltage is between 12 and 20 V/cm (high voltage); and wherein the first frequency is 5 Hz or less (low frequency) and the second frequency is between 15 and 20 Hz (high frequency), d) detecting activation of the nerve cell by detecting the fluorescent dye, e) selecting a therapeutic drug to treat the patient based on the patient's diagnosis and the selectivity of the drug for either Aδ-type nerve cells or C-type nerve cells, thereby customizing the pain treatment for the patient, wherein low voltage and low frequency activation, or low voltage and high frequency activation indicates the nerve cell is a Aδ-type nerve cell, and wherein activation only detected at high voltage indicates the nerve cell is a C-type nerve cell.

In some embodiments, the indicator is a calcium sensitive indicator.

In another aspect, disclosed herein is a method for assessing the potential efficacy of a selected drug for pain patient or a class of patients all exhibiting the same painful symptoms and pain type, the method comprising the steps of: a) measuring the drug's selectivity for Aδ or C fibers, or the lack of selectivity, based on the methods disclosed herein; b) measuring, in a patient or a group of patients, the type of fiber damage employing one or more of the following methods: i) the Neurometer device, ii) quantitative sensory testing, iii) questionnaire-based nerve damage assessment; and c) establishing congruency between the drug selectivity, or lack thereof, for Aδ- and C-fibers and the type of damage observed in the patient, thereby assessing the efficacy of the drug.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (and equivalent open-ended transitional phrases thereof like including, containing and having) encompasses all the expressly recited elements, limitations, steps and/or features alone or in combination with unrecited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amended for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Lastly, the terminology used herein is for the purpose of describing particular embodiments only, and is not intended to limit the scope of the present invention, which is defined solely by the claims. Accordingly, the present invention is not limited to that precisely as shown and described.

What is claimed is:

1. A method of identifying and distinguishing different types of nerve cells in ex vivo cell culture, the method comprising the steps of:
   a. culturing somato-sensory nerve cells ex vivo,
   b. loading the nerve cells with a calcium, sodium, or voltage-sensitive indicator or expressing a genetically encoded calcium, sodium, or voltage-sensitive indicator,
   c. pulsing the nerve cells with an electrical train of bipolar square waves at two different voltages and two different frequencies; wherein the first voltage is 10 V/cm or less (low voltage) and the second voltage is between 12 and 20 V/cm (high voltage); and wherein the first frequency is 5 Hz or less (low frequency) and the second frequency is between 15 and 20 Hz (high frequency), and
   d. detecting activation of the nerve cell by measuring the changes in the signal intensity of the indicator,
   wherein low voltage and low frequency activation indicates a first type of cell and activation detected only at high voltage indicates a second type of cell.

2. The method of claim 1, wherein the nerve cell is a human nerve cell, a rodent nerve cells or a non-human primate nerve cell.

3. The method of claim 1, wherein the indicator is a calcium sensitive indicator.

4. A method of identifying a drug candidate selective for a Aδ-type nerve cell or a C-type nerve cell, the method comprising the steps of:
   a. culturing somato-sensory nerve cells ex vivo,
   b. loading the nerve cells with a calcium, sodium, or voltage-sensitive indicator or expressing a genetically encoded calcium, sodium, or voltage-sensitive indicator,
   c. pulsing the nerve cells with an electrical train of bipolar square waves at two different voltages and two different frequencies; wherein the first voltage is less than 10 V/cm (low voltage) and the second voltage is between 12 and 20 V/cm (high voltage); and wherein the first frequency is less than 5 Hz (low frequency) and the second frequency is between 15 and 20 Hz (high frequency),
   d. detecting activation of the nerve cell by measuring the changes in the signal intensity of the indicator,
   e. contacting the nerve cell with a drug candidate, and
   f. determining if the drug candidate selectively modulates the nerve cell, thereby identifying a drug candidate selective for a Aδ-type nerve cell or a C-type nerve cell,
   wherein low voltage and low frequency activation, or low voltage and high frequency activation indicates the nerve cell is a Aδ-type nerve cells and activation detected only at high voltage indicates the nerve cell is a C-type nerve cell.

5. The method of claim 4, wherein the drug candidate is selected from the group consisting of NSAID, corticosteroid, acetaminophen, opioid, muscle relaxant, anti-anxiety, tricyclic anti-depressant, a local anesthetic, a voltage gated channel inhibitor, and anti-epileptic.

6. The method of claim 4, wherein the drug candidate has not previously been used to treat pain.

7. The method of claim 4, wherein the nerve cell is a human nerve cell, a rodent nerve cell, or a non-human primate nerve cell.

8. The method of claim 4, wherein the indicator is a calcium sensitive indicator.

9. A method of providing a customized pain treatment for a patient in need thereof, the method comprising the steps of:
   a. culturing somato-sensory nerve cells from a patient ex vivo; wherein the patient has a known disease diagnosis,
   b. loading the nerve cells with a calcium, sodium, or voltage-sensitive indicator or expressing a genetically encoded calcium, sodium, or voltage-sensitive indicator,
   c. pulsing the nerve cells with an electrical train of bipolar square waves at two different voltages and two different frequencies; wherein the first voltage is 10 V/cm or less (low voltage) and the second voltage is between 12 and 20 V/cm (high voltage); and wherein the first frequency is 5 Hz or less (low frequency) and the second frequency is between 15 and 20 Hz (high frequency),
   d. detecting activation of the nerve cell by detecting fluorescent dye,
   e. selecting a therapeutic drug to treat the patient based on the patient's diagnosis and the selectivity of the drug for either Aδ-type nerve cells or C-type nerve cells, thereby customizing the pain treatment for the patient,
   wherein low voltage and low frequency activation, or low voltage and high frequency activation indicates the nerve cell is a Aδ-type nerve cell, and wherein activation only detected at high voltage indicates the nerve cell is a C-type nerve cell.

10. The method of claim 9, wherein the indicator is a calcium sensitive indicator.

11. A method for assessing the potential efficacy of a selected drug for pain patient or a class of patients all exhibiting the same painful symptoms and pain type, the method comprising the steps of:
   a. measuring the drug's selectivity for Aδ or C fibers, or the lack of selectivity, using the method of claim 4;
   b. measuring, in a patient or a group of patients, the type of fiber damage employing one or more of the following methods:

i) quantitative sensory testing,
ii) questionnaire-based nerve damage assessment; and
c. establishing congruency between the drug selectivity, or lack thereof, for Aδ- and C-fibers and the type of damage observed in the patient, thereby assessing the efficacy of the drug.

\* \* \* \* \*